United States Patent
Sakuta

(10) Patent No.: US 6,300,283 B1
(45) Date of Patent: Oct. 9, 2001

(54) WATER-BASE AGROCHEMICAL COMPOSITION CONTAINING POLYETHER-MODIFIED SILICONE

(75) Inventor: Koji Sakuta, Gunma-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/572,969

(22) Filed: May 18, 2000

(30) Foreign Application Priority Data

May 19, 1999 (JP) .................................................. 11-138633

(51) Int. Cl.⁷ .................................................. A01N 25/30
(52) U.S. Cl. .......................... 504/362; 504/363; 514/772; 514/937; 514/975
(58) Field of Search .................................. 504/362, 363; 514/772, 937, 975

(56) References Cited

U.S. PATENT DOCUMENTS 4,990,175 * 2/1991 Petroff et al. ............................. 71/92
5,558,806 9/1996 Policello .............................. 252/355

FOREIGN PATENT DOCUMENTS

| 355 650 | 2/1990 | (EP) . |
| 1 255 249 | 12/1971 | (GB) . |
| 89 12394 | 12/1989 | (WO) . |

OTHER PUBLICATIONS

Stevens P J G: "Organosilicone Surfactants as adjuvants for agrochemicals" Pesticide Science, GB, vol. 38, No. 2/03, 1993, pp. 103–122.

* cited by examiner

*Primary Examiner*—S. Mark Clardy
(74) *Attorney, Agent, or Firm*—Millen, White, Zelano & Branigan, P.C.

(57) ABSTRACT

A water-base agrochemical composition containing a polyether-modified organopolysiloxane compound as a spreader is proposed to improve spreadability of the agricultural chemical compound over plants. The polyether-modified organopolysiloxane compound is characterized by a specific weight fraction of the polyoxyethylene units and a specific molecular weight of the compound so as to exhibit high and stable surface activity in an aqueous solution over a wide range of the pH value.

3 Claims, No Drawings

WATER-BASE AGROCHEMICAL COMPOSITION CONTAINING POLYETHER-MODIFIED SILICONE

BACKGROUND OF THE INVENTION

The present invention relates to a novel water-base agrochemical composition containing a unique polyether-modified silicone compound. More particularly, the invention relates to a water-base agrochemical composition containing a unique polyether-modified silicone compound as a spreader agent for the agricultural chemical compound as the effective ingredient in the composition and suitable for spraying over agricultural fields, of which the polyether-modified silicone or organopolysiloxane compound is capable of exhibiting high surface activity in an aqueous medium with good stability over a wide range of the pH value of the water-base agrochemical composition.

It is a very common practice that water-base agrochemical compositions in the form of an aqueous solution or emulsion applied to the plants in the agricultural fields and orchards are almost always formulated with a spreader or tacker in order to improve spreadability of the agrochemical composition with good uniformity over the plants so as to ensure high herbicidal, insecticidal and pesticidal effects.

The spreader agents conventionally formulated in a water-base agrochemical composition are each a surface active agent by which the water-base composition is imparted with a decreased surface tension so as to promote uniform adherence of the agricultural chemical to the body of the plants within a short time. Various types of surface active agents are heretofore proposed and employed as an agrochemical spreader including polyoxyethylene alkyl ethers, polyoxyethylene alkylphenyl ethers and polyoxyethylene higher fatty acid esters.

Besides the above mentioned polyoxyethylene-based surface active agents, silicone-based surface active agents are highlighted in recent years as an agrochemical spreader agent for water-base agrochemical compositions in respect of their high surface activity and low toxicity against human body. For example, Japanese Patent Kokai 6-55642 proposes a silicone-based spreader agent for a water-base agrochemical composition which is an organotrisiloxane compound expressed by the general formula

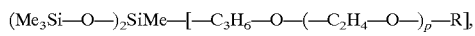

$(Me_3Si-O-)_2SiMe-[-C_3H_6-O-(-C_2H_4-O-)_p-R]$, in which Me is a methyl group, R is a hydrogen atom or a methyl group and the subscript p is a positive integer of 6 to 10.

The applicability of the above defined polyoxyethylene-modified organotrisiloxane compound as an agrochemical spreader agent, however, is very limited because an aqueous solution of the compound exhibits surface activity only when the aqueous solution has a pH at or in the vicinity of neutrality and the surface activity of the aqueous solution thereof is decreased or lost when the solution is acidic or alkaline as is reported in Pesticidal Science, volume 38 (1993), pages 103–122. When the aqueous solution of the silicone compound has a pH value lower than 5 or higher than 9, for example, the surface activity of the aqueous solution is lost within only 24 hours of standing at room temperature. Reportedly, the mechanism for this surface activity degradation is presumably that a siloxane-rearrangement disproportionation reaction takes place in the molecules of the trisiloxane compound resulting in the formation of hexamethyl disiloxane on one hand and a diorganopolysiloxane of a larger molecular weight on the other hand. Accordingly, it is usually important that the spreader-formulated water-base agrochemical composition is prepared by admixing the silicone compound, immediately before use of the composition in the fields, to a master composition or that the pH value of the spreader-formulated water-base composition is kept at or around neutrality by using a suitable buffer solution.

It is sometimes the case, however, that a spreader-formulated water-base agrochemical composition can not always be actually employed just after preparation by the admixture of the silicone compound, for example, due to a sudden change in the weather for raining necessitating postponing of actual application of the ready-prepared composition which must be replaced with a new preparation when the weather is recovered. The use of a buffer solution to ensure neutrality of the water-base composition is also not free from a serious disadvantage because the agricultural chemical compound as the effective ingredient of the water-base composition is necessarily limited to those compounds having stability at neutrality since even weak acidity or weak alkalinity of the water-base composition is detrimental against stability of the compound.

SUMMARY OF THE INVENTION

The present invention accordingly has an object, in view of the above described problems and disadvantages relative to the conventional water-base agrochemical compositions containing a surface active agent as a spreader, to provide a novel spreader-containing water-base agrochemical composition in which the effectiveness of the spreader agent can be retained with stability over a long period of time irrespective of the pH value of the water-base composition in a wide range.

Thus, the spreader-containing water-base agrochemical composition provided by the present invention is a uniform blend which comprises:

(a) water as a solvent or dispersion medium;
(b) a chemical compound capable of exhibiting activity as an agricultural chemical in an effective amount as dissolved or dispersed in water as the component (a); and
(c) a polyether-modified organopolysiloxane compound represented by the general formula

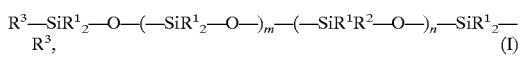

$R^3-SiR^1{}_2-O-(-SiR^1{}_2-O-)_m-(-SiR^1R^2-O-)_n-SiR^1{}_2-R^3$, (I)

In which the subscript m is a positive integer not exceeding 10 and the subscript n is 0 or a positive integer not exceeding 10 with the proviso that m+n is at least 2, $R^1$ is an alkyl group having 1 to 5 carbon atoms or a phenyl group, $R^2$ is a polyoxyalkylene-substituted alkyl group of the general formula $-C_xH_{2x}-O-(C_2H_4O)_y-(C_3H_6O)_z-R^4$, $R^4$ being a hydrogen atom, an alkyl group having 1 to 5 carbon atoms or an acetyl group, the subscript x being a positive integer of 2, 3 or 4, the subscript y being a positive integer of 5 to 15 and the subscript z being 0 or a positive integer not exceeding 10, and $R^3$ is $R^1$ or $R^2$ with the proviso that, when the subscript n is 0, at least one of the two $R^3$ groups in a molecule is $R^2$, of which the molecular weight does not exceed 2000 and the weight fraction of the polyoxyethylene units of the formula $-(C_2H_4O)_y-$ is in the range from 30% to 60% by weight as dissolved in water as the component (a) in an amount in the range from 0.005 to 30% by weight based on the total amount of the water-base composition.

DETAILED DESCRIPTION OF THE PREFERRED EMBODIMENTS

As is described above, the water-base agrochemical composition as the object of the present invention, which has been completed as a result of the inventor's extensive investigations to accomplish the above described object of the invention, comprises, as a uniform blend, (a) water as a medium, (b) an effective amount of an agricultural chemical compound as an effective ingredient dissolved or dispersed in water and (c) a limited amount of a polyether-modified organopoly-siloxane compound having a structure represented by the general formula (I) defined above. This unique formulation of the water-base agrochemical composition has been established on the base of the unexpected discovery by the inventor that a silicone compound can be an excellent spreader in a water-base agrochemical composition as desired when and only when the silicone compound has a molecular structure defined by the general formula (I).

The polyether-modified silicone compound as the component (c), which is the most characteristic ingredient in the inventive water-base agrochemical composition, is an organopolysiloxane represented by the general formula (I) and has a molecular weight not exceeding 2000. When the molecular weight thereof exceeds 2000, the organopolysiloxane compound is inferior as a surface active agent to serve as a spreader agent in a water-base agrochemical composition. Further, it is essential that the weight fraction of the polyoxyethylene units of the formula $-(C_2H_4O)_y-$ in the molecules is in the range from 30 to 60%. When this weight fraction is too small, the organopolysiloxane compound is less soluble in an aqueous medium not to work as a good surface active agent while, when the weight fraction is too large, a decrease is caused also in the surface activity of the organopolysiloxane compound.

The group denoted by $R^1$ in the general formula (I) is a phenyl group or an alkyl group having 1 to 5 carbon atoms exemplified by methyl, ethyl, propyl, butyl and pentyl groups of which methyl group is preferable. The group denoted by $R^2$ in the general formula (I) is a polyoxyalkylene-substituted alkyl group of the formula $-(C_2H_4O)_y-(C_3H_6O)_z-R^4$, in which $R^4$ is a hydrogen atom, an alkyl group of 1 to 5 carbon atoms or an acetyl group and each of the subscripts x, y and z has a value specified above. The group denoted by $R^3$ in the general formula (I) is either $R^1$ or $R^2$ with the proviso that, when the subscript n in the general formula (I) is 0, at least one of the two $R^3$ groups at the molecular chain terminals of the organopolysiloxane molecule is the polyoxyalkylene-substituted alkyl group denoted by $R^2$. This proviso means that the organopolysiloxane compound always has at least one polyoxyalkylene-substituted alkyl group $R^2$ in a molecule as bonded to the silicon atom either at a molecular chain end or at an intermediate position.

The subscript m in the general formula (I) is a positive integer not exceeding 10. When the value of the subscript m is equal to 0, the organopolysiloxane compound is more liable to be influenced by the changes in the pH value of the aqueous medium to lose stability in an acidic or alkaline medium while, when the value of m is too large, the organopolysiloxane compound suffers a decrease in the surface activity because of the poor hydrophilicity of the compound. The subscript n in the general formula (I) is 0 or a positive integer not exceeding 10. When the value of n is too large, the organopolysiloxane compound has an unduly large molecular weight to suffer a decrease in the surface activity.

Although the general formula (I) given above represents an organopolysiloxane molecule having a straightly linear polysiloxane main chain structure, a small amount of branching in the molecular structure has no particular adverse influences on the performance of the organopolysiloxane compound as a spreader agent in a water-base agrochemical composition.

An example of the polyether-modified silicone compounds represented by the general formula (I) and preferable as a spreader agent in a water-base agrochemical composition includes those having a molecular weight not exceeding 1500 and represented by the general formula

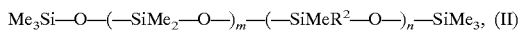

$$Me_3Si-O-(-SiMe_2-O-)_m-(-SiMeR^2-O-)_n-SiMe_3, \quad (II)$$

In which Me is a methyl group and $R^2$ is a polyoxyalkylene-substituted alkyl group of the formula $-C_3H_6-O-(C_2H_4O)_y-(C_3H_6O)_z-R^4$, the subscript z not exceeding 5 and the other symbols each having the same meaning as defined before, of which the weight fraction of the polyoxyethylene units is in the range from 40 to 55%. It is more preferable in the general formula (II) given above that the subscript m is a positive integer of 2 to 5 and the subscript n is 1, 2 or 3. The polyether-modified silicone compounds of this type exhibit and maintain high surface activity in both of an acidic and alkaline aqueous media. When the weight fraction of the polyoxyethylene units is smaller than 40%, the compound suffers a decrease in the stability in an acidic aqueous medium while, when the weight fraction is larger than 55%, a decrease of stability is caused in an alkaline aqueous medium.

An example of preferable polyether-modified organopolysiloxane compounds of a different type includes those having a molecular weight not exceeding 1500 and represented by the general formula

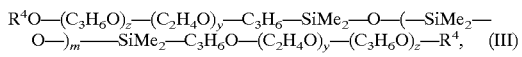

$$R^4O-(C_3H_6O)_z-(C_2H_4O)_y-C_3H_6-SiMe_2-O-(-SiMe_2-O-)_m-SiMe_2-C_3H_6O-(C_2H_4O)_y-(C_3H_6O)_z-R^4, \quad (III)$$

In which the subscript m is a positive integer of 2 to 6 and the subscript z does not exceed 5, the other symbols each having the same meaning as defined for the general formula (I), of which the weight fraction of the polyoxyethylene units is in the range from 40 to 60%.

An example of preferable polyether-modified organopolysiloxane compounds of a still different type includes those having a molecular weight not exceeding 1500 and represented by the general formula

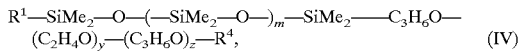

$$R^1-SiMe_2-O-(-SiMe_2-O-)_m-SiMe_2-C_3H_6O-(C_2H_4O)_y-(C_3H_6O)_z-R^4, \quad (IV)$$

In which $R^1$ is an alkyl group having 1 to 5 carbon atoms and the subscript z does not exceed 5, the other symbols each having the same meaning as defined for the general formula (I), of which the weight fraction of the polyoxyethylene units is in the range from 40 to 55%.

An example of preferable polyether-modified organopolysiloxane compounds of a further different type includes those represented by the general formula

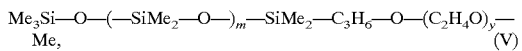

$$Me_3Si-O-(-SiMe_2-O-)_m-SiMe_2-C_3H_6-O-(C_2H_4O)_y-Me, \quad (V)$$

In which the subscript m is 2, 3 or 4 and the subscript y is a positive integer of 6 to 12.

The above described various types of the polyether-modified organopolysiloxane compounds can be employed as a spreader agent in a water-base agrochemical composition to exhibit high and stable surface activity regardless of the types of the agricultural chemicals and acidity or alkalinity of the aqueous medium. In the preparation of a water-base agrochemical composition by compounding the polyether-modified organopolysiloxane compound, it is optional that the water-base composition under preparation is admixed with a defoaming agent such as silicone-based defoaming agents as a combination of a silicone oil and a fine silica powder with an object to overcome the troubles due to foaming. The amount of the spreader compound in the inventive water-base agrochemical composition is in the range from 0.005 to 30% by weight or, preferably, from 0.005 to 1% by weight based on the amount of the composition. It is of course within the scope of the invention that a commercial agricultural chemical composition containing the silicone compound in a higher concentration is prepared in the producer and the commercial product is diluted with water before application of the water-base composition by the respective consumers to give the above mentioned concentration of the spreader.

In the following, the present invention is described in more detail by way of non-limitative examples by way of a description of the performance of the specific polyether-modified silicone compound as a surface active agent, in which the values of the surface tension in aqueous solutions are all those obtained by the measurement at 25° C. for an aqueous solution of a specified concentration of the compound. As a criterion for the evaluation of the surface active agent as a spreader agent in a water-base agrochemical composition, it is taken that the surface active agent can be used as the spreader agent when the surface tension of an aqueous solution thereof determined in the above mentioned manner does not exceed 30 mN/m from the practical standpoint.

EXAMPLE 1

A polyether-modified organopolysiloxane compound expressed by the general formula $$Me_3Si\text{—}O\text{—}(\text{—}SiMe_2\text{—}O\text{—})_m\text{—}(\text{—}SiMeG\text{—}O\text{—})_n\text{—}SiMe_3, \quad (VI)$$

In which Me was a methyl group, G is a polyoxyalkylene-substituted alkyl group of the formula $\text{—}C_3H_6\text{—}(C_2H_4O)_y\text{—}(C_3H_6O)_z\text{—}R$, R being a hydrogen atom, y being 10 and z being 0, the subscript m was 3 and the subscript n was 1 in this Example, of which the weight fraction of the polyoxyethylene units was 46.7%, was dissolved in a concentration of 0.01% by weight in an aqueous solution having a pH of 4.0 or 10.0 as adjusted with an aqueous solution of hydrochloric acid or sodium hydroxide, respectively. A 0.01% by weight aqueous solution of the same silicone compound prepared by using deionized water had a surface tension, referred to as $\gamma_n$ hereinafter, of 25.5 mN/m at 25° C.

Each of the acidic and alkaline aqueous solutions of the silicone prepared above was kept standing at room temperature with periodical measurements of the surface tension after 1, 3, 7, 14 and 30 days of standing to give the results shown in the unit of mN/m in Tables 2 and 3 for the acidic and alkaline solutions, respectively, in which $\gamma_1, \gamma_3, \gamma_7, \gamma_{14}$ and $\gamma_{30}$ are each the surface tension of the aqueous solution after standing of 1, 3, 7, 14 and 30 days, respectively. The "change rate" in % given in the right end column of the Tables is a value calculated by the equation:

$$\text{Change rate, \%} = (\gamma_{30} - \gamma_n)/\gamma_n \times 100,$$

In which $\gamma_{30}$ is the surface tension of the solution after 30 days of standing and $\gamma_n$ is the surface tension of the neutral solution of the same surface active agent as prepared.

EXAMPLES 2 TO 5 AND COMPARATIVE EXAMPLES 1 TO 6

Acidic and alkaline aqueous test solutions were prepared in each of these Examples and Comparative Examples in the same formulation as in Example 1 except that the polyether-modified silicone compound used therein, which was represented by the general formula (VI) given in Example 1, was characterized by the values of the subscripts m, n, y and z as well as the group denoted by R, molecular weight MW and the weight fraction of the polyoxyethylene units EO% summarized in Table 1 together with the corresponding parameters of the silicone compound used in Example 1.

The results of the surface tension measurements are shown in Tables 2 and 3 for the acidic and alkaline aqueous solutions, respectively, together with the values of $\gamma_n$ for a neutral solution. The values of the change rate, %, for Comparative Examples 1 and 2 in Table 2 were calculated by using the same equation excepting for the replacement of $\gamma_{30}$ with $\gamma_1$. The values of the change rate, %, for Comparative Examples 1 and 2 in Table 3 were calculated by using the same equation excepting for the replacement of $\gamma_{30}$ with $\gamma_{14}$.

TABLE 1

| | m | n | y | z | R | MW | EO % |
|---|---|---|---|---|---|---|---|
| Example 1 | 3 | 1 | 10 | 0 | H | 942 | 46.7 |
| Example 2 | 3 | 1 | 10 | 1 | $CH_3$ | 1014 | 43.4 |
| Example 3 | 3 | 2 | 10 | 0 | H | 1500 | 58.7 |
| Example 4 | 3 | 1 | 6 | 0 | $CH_3$ | 780 | 33.8 |
| Example 5 | 4 | 2 | 9 | 0 | H | 1486 | 53.3 |
| Comparative Example 1 | 0 | 1 | 6 | 0 | $CH_3$ | 558 | 47.3 |
| Comparative Example 2 | 0 | 2 | 6 | 0 | $CH_3$ | 954 | 55.3 |
| Comparative Example 3 | 10 | 5 | 10 | 0 | $CH_3$ | 3762 | 58.5 |
| Comparative Example 4 | 27 | 3 | 20 | 20 | $CH_3$ | 8802 | 30.0 |
| Comparative Example 5 | 24 | 4 | 10 | 0 | H | 4170 | 42.2 |
| Comparative Example 6 | 10 | 3 | 6 | 0 | H | 2048 | 38.7 |

TABLE 2

| | $\gamma_n$ | $\gamma_1$ | $\gamma_3$ | $\gamma_7$ | $\gamma_{14}$ | $\gamma_{30}$ | Change rate, % |
|---|---|---|---|---|---|---|---|
| Example 1 | 25.5 | 23.8 | 25.9 | 25.8 | 26.6 | 28.0 | +9.8 |
| Example 2 | 25.0 | 24.3 | 25.3 | 25.0 | 25.5 | 25.5 | +2.0 |
| Example 3 | 28.9 | 29.9 | 31.5 | 32.3 | 31.8 | 34.4 | +19.0 |
| Example 4 | 27.8 | 27.4 | 27.6 | 28.6 | 28.1 | 29.2 | +5.0 |
| Example 5 | 26.7 | 26.9 | 27.1 | 28.0 | 28.7 | 29.4 | +10.1 |
| Comparative Example 1 | 21.7 | 45.4 | — | — | — | — | +97.4 |
| Comparative Example 2 | 23.1 | 46.2 | — | — | — | — | +100.0 |
| Comparative Example 3 | 29.7 | 29.7 | 29.7 | 30.8 | 30.1 | 31.1 | +4.7 |
| Comparative Example 4 | 39.8 | 35.1 | 37.5 | 36.9 | 35.7 | 37.1 | −6.8 |
| Comparative Example 5 | 39.4 | 33.7 | 37.8 | 38.7 | 39.4 | 38.2 | −3.0 |
| Comparative Example 6 | 29.3 | 30.0 | 30.6 | 30.4 | 31.0 | 31.6 | +7.8 |

TABLE 3

| | $\gamma_n$ | $\gamma_1$ | $\gamma_3$ | $\gamma_7$ | $\gamma_{14}$ | $\gamma_{30}$ | Change rate, % |
|---|---|---|---|---|---|---|---|
| Example 1 | 25.5 | 24.4 | 25.1 | 24.9 | 26.2 | 26.8 | +5.1 |
| Example 2 | 25.0 | 23.9 | 25.2 | 25.0 | 27.4 | 26.4 | +5.6 |
| Example 3 | 28.9 | 27.8 | 28.4 | 28.6 | 28.8 | 29.2 | +1.0 |

TABLE 3-continued

|  | $\gamma_n$ | $\gamma_1$ | $\gamma_3$ | $\gamma_7$ | $\gamma_{14}$ | $\gamma_{30}$ | Change rate, % |
|---|---|---|---|---|---|---|---|
| Example 4 | 27.8 | 28.9 | 29.1 | 27.4 | 30.2 | 31.6 | +13.7 |
| Example 5 | 26.7 | 26.8 | 27.0 | 27.6 | 28.0 | 28.8 | +7.9 |
| Comparative Example 1 | 21.7 | 30.5 | 36.2 | 42.8 | 48.7 | — | +112.0 |
| Comparative Example 2 | 23.1 | 30.5 | 38.4 | 45.0 | 51.1 | — | +121.0 |
| Comparative Example 3 | 29.7 | 28.2 | 28.8 | 28.8 | 30.5 | 31.5 | +6.1 |
| Comparative Example 4 | 39.8 | 37.2 | 37.2 | 38.4 | 38.2 | 39.4 | −1.0 |
| Comparative Example 5 | 39.4 | 36.1 | 36.0 | 34.9 | 39.4 | 41.1 | +4.3 |
| Comparative Example 6 | 29.3 | 31.4 | 32.3 | 31.7 | 33.0 | 33.4 | +14.0 |

EXAMPLES 6 TO 11 AND COMPARATIVE EXAMPLES 7 AND 8

The experimental procedure in each of these Examples and Comparative Examples was about the same as in Example 1 except that:

the polyether-modified silicone compound was represented by the general formula

HO—(C$_3$H$_6$O)$_z$—(C$_2$H$_4$O)$_y$—C$_3$H$_6$—SiMe$_2$—O—(—SiMe$_2$—O—)$_p$—SiMe$_2$—C$_3$H$_6$—O—(C$_2$H$_4$O)$_y$—(C$_3$H$_6$O)$_z$—H,  (VII)

In which the subscripts p, y and z were as shown in Table 4 together with the molecular weight MW and the weight fraction of the polyoxyethylene units EO% in the silicone compound;

the concentration of the silicone compound in the acidic and alkaline solutions of pH 4.0 and 10.0, respectively, was 0.1% by weight instead of 0.01% by weight; and the aqueous silicone solutions were kept standing at 70° C. instead of room temperature.

The results of the surface tension measurements at 25° C. are shown in Table 5 for the acidic (pH=4.0) and alkaline (pH=10.0) solutions giving, together with the values of $\gamma_n$, i.e. the initial surface tension of a neutral solution prepared with deionized water, $\gamma_2$ and $\gamma_5$, i.e. the surface tensions of the solutions after 2 days and 5 days standing, respectively, and the change rate, %, which was calculated by using $\gamma_5$ instead of $\gamma_{30}$ in Example 1. The change rate, %, for Comparative Examples 7 and 8 in an acidic solution was calculated with $\gamma_2$ instead of $\gamma_5$.

TABLE 4

|  | p | y | z | MW | EO % |
|---|---|---|---|---|---|
| Comparative Example 7 | 0 | 6 | 0 | 778 | 67.9 |
| Comparative Example 8 | 1 | 6 | 0 | 852 | 62.0 |
| Example 6 | 2 | 6 | 0 | 926 | 57.0 |
| Example 7 | 3 | 6 | 0 | 1000 | 52.8 |
| Example 8 | 4 | 6 | 0 | 1074 | 49.2 |
| Example 9 | 5 | 6 | 0 | 1148 | 46.0 |
| Example 10 | 6 | 6 | 0 | 1222 | 43.2 |
| Example 11 | 4 | 8 | 2 | 1482 | 47.5 |

TABLE 5

|  |  | pH = 4.0 | | | pH = 10.0 | |
|---|---|---|---|---|---|---|
|  | $\gamma_n$ | $\gamma_2$ | $\gamma_5$ | Change rate, % | $\gamma_2$ | $\gamma_5$ | Change rate, % |
| Comparative Example 7 | 42.8 | 52.0 | — | +21.5 | 45.3 | 54.3 | +26.9 |
| Comparative Example 8 | 25.6 | 51.6 | — | +101.6 | 26.4 | 56.7 | +121.5 |
| Example 6 | 22.4 | 24.4 | 26.0 | +16.1 | 23.0 | 24.9 | +11.2 |
| Example 7 | 22.4 | 23.4 | 23.5 | +4.9 | 23.5 | 23.6 | +5.4 |
| Example 8 | 23.1 | 22.9 | 22.8 | −1.3 | 23.2 | 23.5 | +1.7 |
| Example 9 | 22.6 | 22.9 | 23.1 | +2.2 | 23.0 | 23.1 | +2.2 |
| Example 10 | 27.9 | 24.3 | 23.3 | −16.5 | 25.6 | 24.1 | −13.6 |
| Example 11 | 24.2 | 24.4 | 25.2 | +4.1 | 24.6 | 24.8 | +2.5 |

EXAMPLES 12 TO 19 AND COMPARATIVE EXAMPLE 9

The experimental procedure in each of these Examples and Comparative Example was about the same as in Example 1 except that:

the polyether-modified silicone compound was represented by the general formula

A$^1$—SiMe$_2$—O—(—SiMe$_2$—O—)$_p$—SiMe$_2$—C$_3$H$_6$—O—(C$_2$H$_4$O)$_y$—(C$_3$H$_6$O)$_z$—A$^2$,  (VIII)

In which the subscripts p, y and z and the terminal groups A$^1$ and A$^2$ were as shown in Table 6 together with the molecular weight MW and the weight fraction of the polyoxyethylene units EO% in the silicone compound;

the concentration of the silicone compound in the acidic and alkaline solutions of pH 4.0 and 10.0, respectively, was 0.1% by weight instead of 0.01% by weight; and the aqueous silicone solutions were kept standing at 70° C. instead of room temperature.

The results of the surface tension measurements at 25° C. are shown in Table 7 for the acidic (pH=4.0) and alkaline (pH=10.0) solutions giving, together with the values of $\gamma_n$, i.e. the initial surface tension of a neutral solution prepared with deionized water, $\gamma_2$ and $\gamma_5$, i.e. the surface tensions of the solutions after 2 days and 5 days standing, respectively, and the change rate, %, which was calculated by using $\gamma_5$ instead of $\gamma_{30}$ in Example 1.

TABLE 6

|  | A$^1$ | p | y | z | A$^2$ | MW | EO % |
|---|---|---|---|---|---|---|---|
| Comparative Example 9 | C$_4$H$_9$ | 0 | 3 | 0 | H | 380 | 34.7 |
| Example 12 | C$_4$H$_9$ | 1 | 6 | 0 | H | 586 | 45.1 |
| Example 13 | C$_4$H$_9$ | 2 | 8 | 0 | H | 748 | 47.1 |
| Example 14 | C$_4$H$_9$ | 3 | 9 | 0 | H | 866 | 45.7 |
| Example 15 | C$_4$H$_9$ | 4 | 12 | 0 | H | 1072 | 49.3 |
| Example 16 | C$_4$H$_9$ | 5 | 15 | 0 | H | 1278 | 51.6 |
| Example 17 | CH$_3$ | 3 | 11 | 0 | CH$_3$ | 926 | 52.3 |
| Example 18 | CH$_3$ | 3 | 8 | 0 | CH$_3$ | 794 | 44.3 |
| Example 19 | CH$_3$ | 3 | 11 | 2 | CH$_3$ | 1042 | 46.4 |

TABLE 7

| | $\gamma_n$ | pH = 4.0 | | | pH = 10.0 | | |
|---|---|---|---|---|---|---|---|
| | | $\gamma_2$ | $\gamma_5$ | Change rate, % | $\gamma_2$ | $\gamma_5$ | Change rate, % |
| Comparative Example 9 | 24.0 | 24.8 | 30.5 | +27.1 | 23.0 | 23.4 | −2.5 |
| Example 12 | 22.3 | 22.1 | 22.3 | ±0 | 22.3 | 22.3 | ±0 |
| Example 13 | 22.0 | 21.8 | 22.3 | +1.4 | 22.0 | 22.6 | +2.7 |
| Example 14 | 22.0 | 22.0 | 22.4 | +1.8 | 23.5 | 28.8 | +30.9 |
| Example 15 | 22.5 | 23.9 | 25.4 | +12.9 | 30.7 | 35.5 | +57.8 |
| Example 16 | 27.3 | 27.4 | 27.5 | +0.7 | 42.1 | 43.8 | +60.4 |
| Example 17 | 20.0 | 20.0 | 20.1 | +0.5 | 20.0 | 20.2 | +1.0 |
| Example 18 | 20.4 | 20.6 | 20.8 | +2.0 | 20.4 | 20.5 | +0.5 |
| Example 19 | 21.5 | 21.5 | 21.4 | −0.5 | 21.6 | 21.7 | +0.9 |

The above described experimental results support the following conclusions. For example, the surface tension of an aqueous solution of the silicone compound in Comparative Example 1 is greatly decreased in the lapse of time in both of the acidic and alkaline solutions presumably due to the lack in the content of the dimethylsiloxane units. Comparison of Example 3 with Comparative Examples 3 to 6 suggests the influence of the molecular weight on the surface activity which is impractical when the molecular weight exceeds 2000. The surface activity of the silicone compound in Example 3 is unstable in an acidic solution though good in an alkaline solution and vice versa in Example 4. These facts lead to a conclusion that good and stable surface activity can be obtained in both of the acidic and alkaline solutions when the weight fraction of the polyoxyethylene units in the molecule is in the range from 40 to 55% assuming that the silicone compound is modified with the polyoxyalkylene groups on the side chains.

What is claimed is:

1. A water-base agrochemical composition which comprises, as a uniform blend:

(a) water as a solvent or dispersion medium;

(b) a chemical compound capable of exhibiting activity as an agricultural chemical in an effective amount as dissolved or dispersed in water as the component (a); and (c) a polyether-modified organopolysiloxane compound represented by the general formula

$G^2$—SiMe$_2$—O—(—SiMe$_2$—O—)$_{m2}$—SiMe$_2$—$G^2$, wherein Me is a methyl group, the subscript m2 is a positive integer of 2 to 6, and $C^2$ is a polyoxyalkylene-substituted propyl group of the formula —C$_3$H$_6$—O—(C$_2$H$_4$O)$_{y2}$—(C$_3$H$_6$O)$_{y2}$—R$^4$, R$^4$ being a hydrogen atom, an alkyl group having 1 to 5 carbon atoms or an acetyl group, the subscript y$_2$ being a positive integer of 5 to 15 and the subscript z2 being 0 or a positive integer of 5 to 15 and the subscript z2 being 0 or a positive integer not exceeding 5, having a molecular weight not exceeding 1500, of which the weight fraction of the polyoxyethylene units is in the range from 40 to 60%.

2. A water-base agrochemical composition which comprises, as a uniform blend:

(a) water as a solvent or dispersion medium;

(b) a chemical compound capable of exhibiting activity as an agricultural chemical in an effective amount as dissolved or dispersed in water as the component (a); and (c) a polyether-modified organopolysiloxane compound represented by the general formula

R$^{13}$—SiMe$_2$—O—(—SiMe$_2$—O—)$_{m3}$—SiMe$_2$—$G^3$, wherein Me is a methyl group, R$^{13}$ is an alkyl group having 1 to 5 carbon atoms, the subscript m$_3$ is a positive integer not exceeding 6 and $G^3$ is a polyoxyalkylene-substituted propyl group of the formula —C$_3$H$_6$—O—(C$_2$H$_4$O)$_{y3}$—(C$_3$H$_6$O)$_{z3}$—R$^4$, R$^4$ being a hydrogen atom, an alkyl group having 1 to 5 carbon atoms or an acetyl group, the subscript y3 being a positive integer of 5 to 15 and the subscript z3 being 0 or a positive integer not exceeding 5, having a molecular weight not exceeding 1500, of which the weight fraction of the polyoxyethylene units is in the range from 40 to 55%.

3. A water-base agrochemical composition which comprises, as a uniform blend:

(a) water as a solvent or dispersion medium;

(b) a chemical compound capable of exhibiting activity as an agricultural chemical in an effective amount as dissolved or dispersed in water as the component (a); and (c) a polyether-modified organopolysiloxane compound represented by the general formula

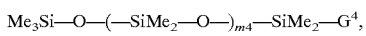

Me$_3$Si—O—(—SiMe$_2$—O—)$_{m4}$—SiMe$_2$—$G^4$, wherein Me is a methyl group, the subscript m4 is a positive integer of 2, 3, or 4 and $G^4$ is a polyoxyalkylene-substituted propyl group of the formula —C$_3$H$_6$—O—(C$_2$H$_4$O)$_{y4}$—Me, the subscript y4 being a positive integer of 6 to 12, having a molecular weight not exceeding 2000, of which the weight fraction of the polyoxyethylene units is in the range of from 40 to 60%.

* * * * *